United States Patent [19]

Hurson

[11] 4,048,987
[45] Sept. 20, 1977

[54] SURGICAL AID

[76] Inventor: James Kevin Hurson, 14 Second St., Orangeville, Ontario, Canada

[21] Appl. No.: 492,208

[22] Filed: July 26, 1974

[30] Foreign Application Priority Data
Aug. 6, 1973 United Kingdom ............... 37278/73
June 28, 1974 Canada ................................... 203740

[51] Int. Cl.² ............................................ A61B 17/02
[52] U.S. Cl. ..................................................... 128/20
[58] Field of Search ..................... 128/20, 303 R, 341, 128/3

[56] References Cited
U.S. PATENT DOCUMENTS

| | | | |
|---|---|---|---|
| 1,944,009 | 1/1934 | Hommer | 128/20 |
| 1,963,173 | 6/1934 | Morin | 128/20 |
| 3,288,131 | 11/1966 | Garland | 128/20 |
| 3,522,799 | 8/1970 | Gauthier | 128/20 |
| 3,522,800 | 8/1970 | Lesser | 128/20 |
| 3,570,475 | 3/1971 | Weinstein | 128/20 |
| 3,572,326 | 3/1971 | Jensen | 128/20 |

OTHER PUBLICATIONS

"A Padded Brain Retractor", Portnoy & Croissant, vol. 1, Surgical Neurology 243, July 1973.
Sales Literature by Heyer-Schulte Corp., Feb. 1974.
Downs Surgical Group Sales Brochure 1973.

Primary Examiner—Robert W. Michell
Assistant Examiner—Henry S. Layton
Attorney, Agent, or Firm—Irving Kayton

[57] ABSTRACT

A surgical aid for retaining displaced material in a surgical site in its displaced position. The aid consists of a wire core of aluminum or aluminum alloy or stainless steel and a covering of a suitable elastomer, such as dimethyl polysiloxane polymer, organo-metallically bonded or otherwise contiguous thereto. The aid is malleable, non-toxic and compatible with cell metabolism. It can be clamped to a retractor frame fixed relative to a surgical site and has major advantages over the use of sponges, towels and other surgical aids now in use. The aid has a body portion and a handle portion which can be held by an assistant or clamped to the frame, allowing the assistant to assume a more productive role in the operation or dispensing with him completely.

46 Claims, 19 Drawing Figures

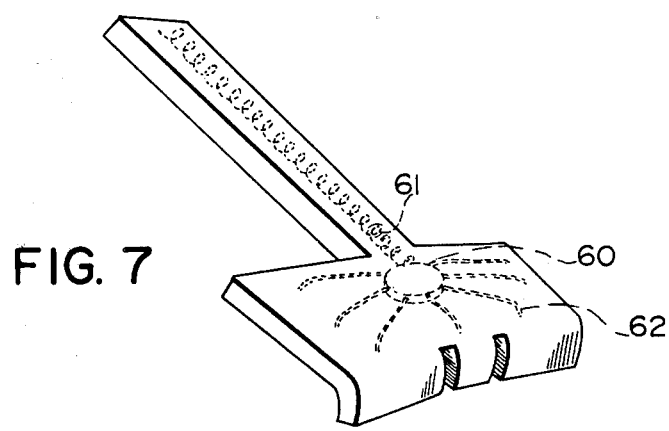
FIG. 7
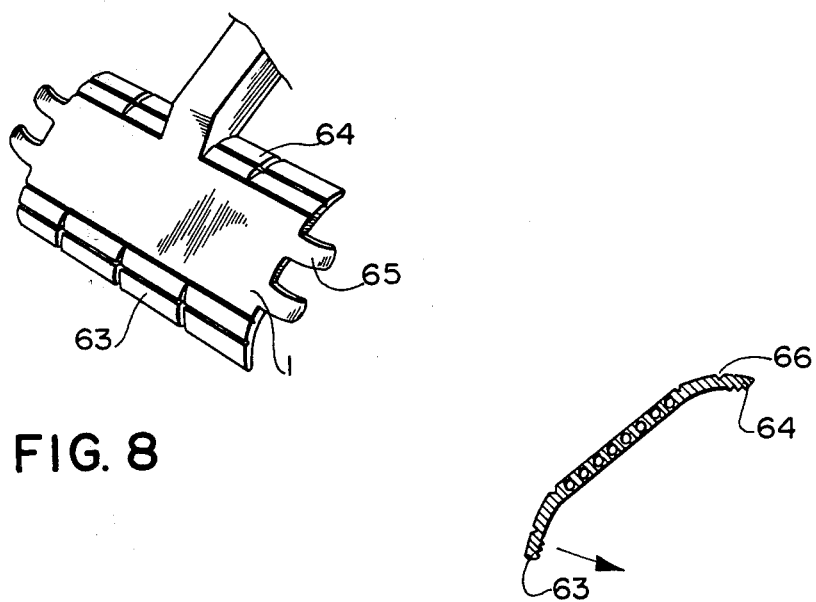
FIG. 8
FIG. 9

SURGICAL AID

BACKGROUND OF THE INVENTION

This invention relates to surgical aids for use in displacing material such as non-skeletal soft tissue, muscles, organs and the like to permit access to a surgical site and to retain such material in displaced position while the surgical operation is proceeding.

The normal procedure today in hospital operating theatres is to have a surgeon's assistant displace material by hand from the surgical site, as called for by the surgeon, the assistant, of course, wearing surgical gloves and perhaps using sponges or towels or hand-held rigid metal instruments against the displaced material.

It is an object of the present invention to eliminate the need for use of the assistant's hands, thus freeing the assistant to assume a more productive role in the operation or completely dispensing with the need for the assistant, as the case may be. It is to be understood, however, that the surgical aids of the present invention are not limited to use in hospital operating theatres but may be adapted for use in dental surgery or veterinary surgery.

It is another object of the present invention to provide a surgical aid which will have minimal adverse effects on he material displaced thereby, as opposed, for example, to towels or sponges which, by virtue of their rough surface, can damage the serosal surface or organs with which they are in engagement. The towels and sponges can also cause drying of the serosal surface by absorption, thereby changing the normal physiology of the organ. Also, the towels and sponges often do not adequately protect the serosal surface from exposure to air, which also causes drying. The aids of the present invention do not suffer from any of these disadvantages nor from the disadvantages exhibited by other surgical aids which have been proposed hitherto but have not come into common use. May of such previous devices cannot be repeatedly bent into various shapes, or they do not maintain the shape to which they are bent, or they react with the body fluids or the serosal covering, or they absorb the body fluids, causing drying, or they have a relatively rough or hard surface which can damage the organ, or they exert too much pressure on the displaced and retained organs, or they deteriorate too rapidly with use, or they are not adapted to be supported externally and therefore do not remain stationary.

SUMMARY OF THE INVENTION

Basically the present invention is a surgical aid comprising a body in the form of a ductile component linked to an elastomeric component, the said body being malleable, non-toxic and compatible with cell metabolism, and a handle extending from said body and also being in the form of a ductile component linked to an elastomeric component, the said handle being malleable, non-toxic and compatible with cell metabolism, whereby the body may be placed in a surgical site to displace and retain tissue not being operated upon and the handle may be grasped at a point outside of the surgical site to maintain the body of the surgical aid in a desired position during the operation, the combined body and handle having a function approximating that of a human hand, wrist and forearm.

Preferably, said body and handle are constituted by a metallic core and an elastomeric covering. The core metal is preferably aluminum or an alloy thereof or stainless steel and the elastomer of the covering is capable of being organo-metallically bonded thereto, the presently preferred elastomer being dimethyl polysiloxane polymer.

The metallic core may be in the form of a plurality of wires intertwined in the handle and forming loops in the body. Alternatively, it may be in the form of a solid piece of metal in the body, a coiled wire extending form the solid piece into the handle and a plurality of wires, which may taper outwardly for increased malleability, radiating from the solid piece into the body.

The aid may be made in various different shapes for use in different operations and the gauge of metal used for the core may be selected to give the most appropriate strength to the aid for the operation for which it is intended. Moreover, the body of the aid may be provided with a soft edge portion or flaps to avoid bruising of material in the surgical site with which the edge of the aid might come in contact. Such flaps may be grooved on one face to make it easier to move them in one direction than in the opposite direction and they may be provided with small ridges to provide finger grips for the surgeon to facilitate his manipulation thereof. In other cases, the body of the aid, at a region remote from the handle, may be subdivided to form fingers which are individually movable and will maintain the relative positions to which they are moved to adapt to the anatomy in the surgical site. Such fingers may also be provided with small ridges as aforesaid.

It is contemplated that, to facilitate manipulation of the body of the aid within the surgical site, controls such as Bowden cables may be built into the aid. It is also contemplated that a suction device and/or a light source may be built in, if desired.

The body of the surgical aid may be held in position in the surgical site by grasping its handle at a position outside of the site, thus giving the surgeon free access to the site and allowing him to manoeuvre the aid as he desires. Such grasping may be effected manually by the surgeon's assistant but it is preferred, in most instances, to have the handle held by a clamp on a retractor frame adapted to be fixed relative to the surgical site. Said frame preferably comprises first, second and third frame members fixed relative to each other with the second and third members spaced apart and extending in parallel in the same direction away from said first member, and a fourth member mounted on said second and third frame members for adjustment toward and away from said first frame member, releasable locking members holding said fourth frame member, in use, away from said first frame member, each of said first and fourth frame members having mounted thereon a pair of retractor hooks longitudinally slidably mounted thereon and at least one of said second and third frame members having a said clamp adjustably mounted thereon.

The slidable mounting of the hooks on the frame permits the surgeon great leeway in his choice of the configuration of the wound permitting access to the surgical site. In some instances he may wish a narrow configuration but in others he may prefer an almost circular configuration. The engagement of the retractor hooks by the musculature surrounding the wound retains the locking members in locking position and holds the frame in a fixed position relative to the surgical site, thus ensuring that the body of the surgical aid will maintain its position in the site during the operation unless adjusted by the surgeon.

BRIEF DESCRIPTION OF DRAWINGS

Embodiments of the present invention will now be described, by way of example, with reference to the accompanying drawings, in which:

FIG. 7 is a view of a surgical aid having a different core construction than those shown in FIG. 3;

FIG. 8 is a perspective view of another embodiment of the surgical aid of the present invention;

FIG. 9 is a cross-sectional view of the body of the surgical aid shown in FIG. 8.

DESCRIPTION OF PREFERRED EMBODIMENTS

Figure 1:
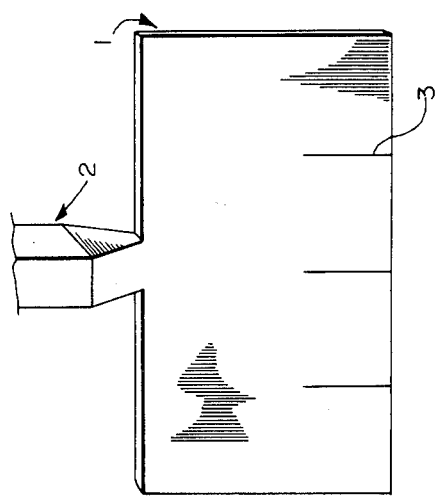
FIG. 1 is a perspective view of a surgical aid.

As shown in FIG. 1 a surgical aid according to the invention has a body portion 1 and a handle portion 2. Both of these are made of an inner core of metal, such as aluminum alloy, and an outer covering of an elastomer such as dimethyl polysiloxane polymer, the two being organo-metallically bonded or otherwise contiguous to each other. Consequently, there are no cavities within the aid and the ductile and resilient properties of the two components are blended. The dimethyl polysiloxane polymer is well known for its compatibility with cell metabolism and, by virtue of its chemically inert nature, it will not sustain micro-organisms in the event that it is accidentally cut or punctured. Moreover, it easily withstands repeated sterilization and is a poor conductor of heat and electricity, all of which make it ideal for the present purposes, although, of course, other elastomers may be quite satisfactory.

Figure 2:
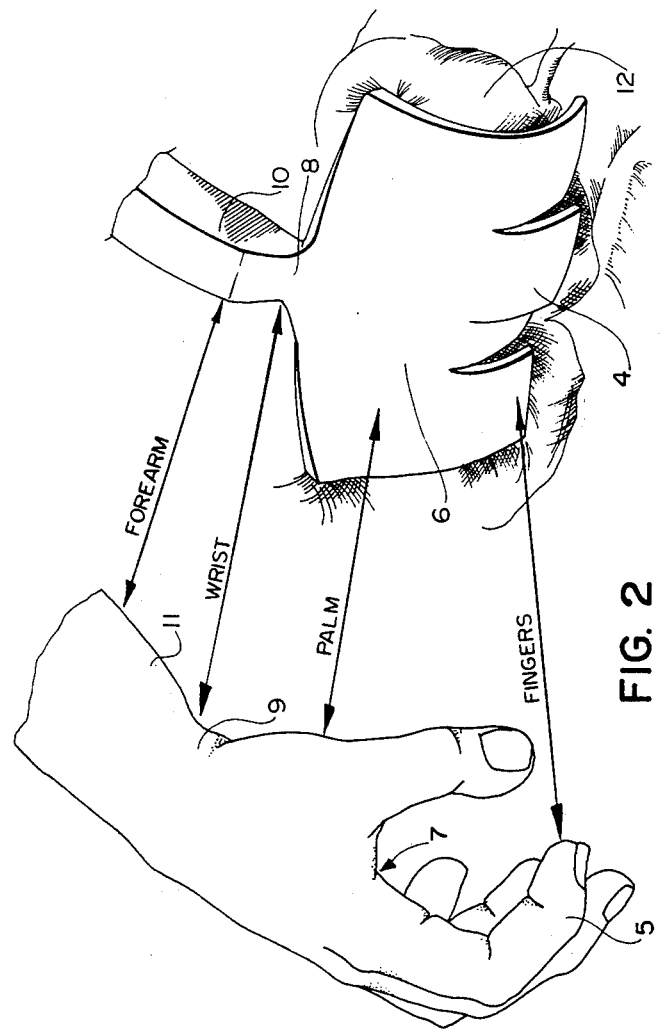
FIG. 2 shows the surgical aid of FIG. 1 in use in a surgical site and also shows a human hand, wrist and forearm to illustrate graphically the similarity in function.

FIG. 2 illustrates the functional similarity of the surgical aid and the human hand, wrist and forearm. Although the aid need not in some cases have the slits 3 subdividing the lower edge of the body portion, these serve in the present embodiment to illustrate even more graphically the aforesaid similarity. Thus, the portions 4 defined by slits 3 can be compared with the human fingers 5, the part 6 above the portions 4 can be compared with the human palm 7, the junction 8 between the body 1 and handle 2 can be compared with the wrist 9 and the portion 10 of the handle adjacent the junction 8 can be compared with the portion 11 of the forearm adjacent the wrist. In addition, the aid has the advantage that the handle can be bent whereas the human forearm can not.

Figure 6:
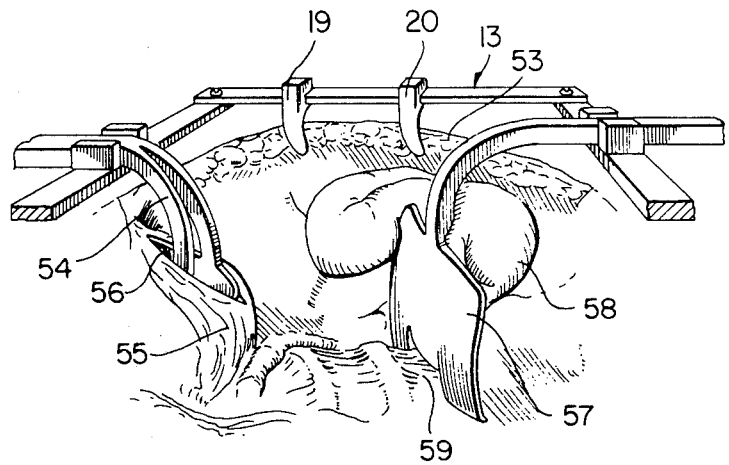
FIG. 6 is a perspective view of a surgical site, showing two different types of surgical aid in use.

The entire aid can be straight, as in FIG. 1, or its various parts can be moved to any of various positions, such as those shown in FIG. 2 and FIG. 6, and they will retain such positions until forcibly displaced therefrom. Thus, the surgeon can manipulate the various parts within the surgical site to give him the exact positions that he wants in order to properly retain and shield the displaced material 12.

Figure 3:
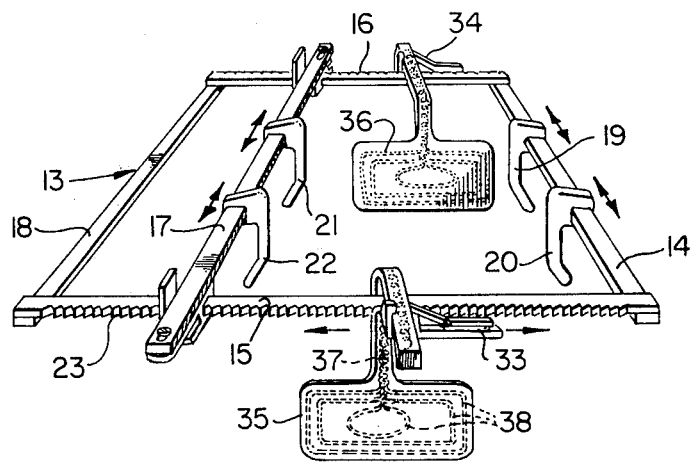
FIG. 3 is a perspective view of a retractor frame having two surgical aids clamped thereto.

The aid can be held by grasping the handle at a position outside of the surgical site with the body extending into the surgical site, thus providing minimum interference with the space available in the surgical site. Such grasping may be done by the hand of an assistant, but in most cases it is preferred that the grasping be done by means of a clamp mounted on a frame which is adapted to be held in fixed relation to the surgical site, thus freeing the surgeon's assistant for a more productive role in the operation, or dispensing with the need for such assistant entirely. As shown in FIG. 3, the frame 13 comprises a first member 14, second and third members 15 and 16, a fourth member 17 and a fifth member 18. The members 14, 15, 16 and 18 form a fixed rectangle whereas the member 17 is movable along members 15 and 16 between members 14 and 18. A pair of retractor hooks 19 and 20 are mounted on member 14 for frictional sliding movement longitudinally thereof and a similar pair of retractor hooks 21 and 22 are likewise frictionally slidably mounted on member 17, such retractor hooks being adapted to engage the edges of a surgical incision and retain same in an open condition to allow the surgeon access to the surgical site. By virtue of the slidable mounting of the four hooks the surgeon may expand the incision to form an open wound of any desired configuration. Thus by having the hooks in each pair close together he can have an elongated wound configuration or, by spacing the hooks relatively far apart, he can achieve an almost circular wound configuration.

Figure 5:
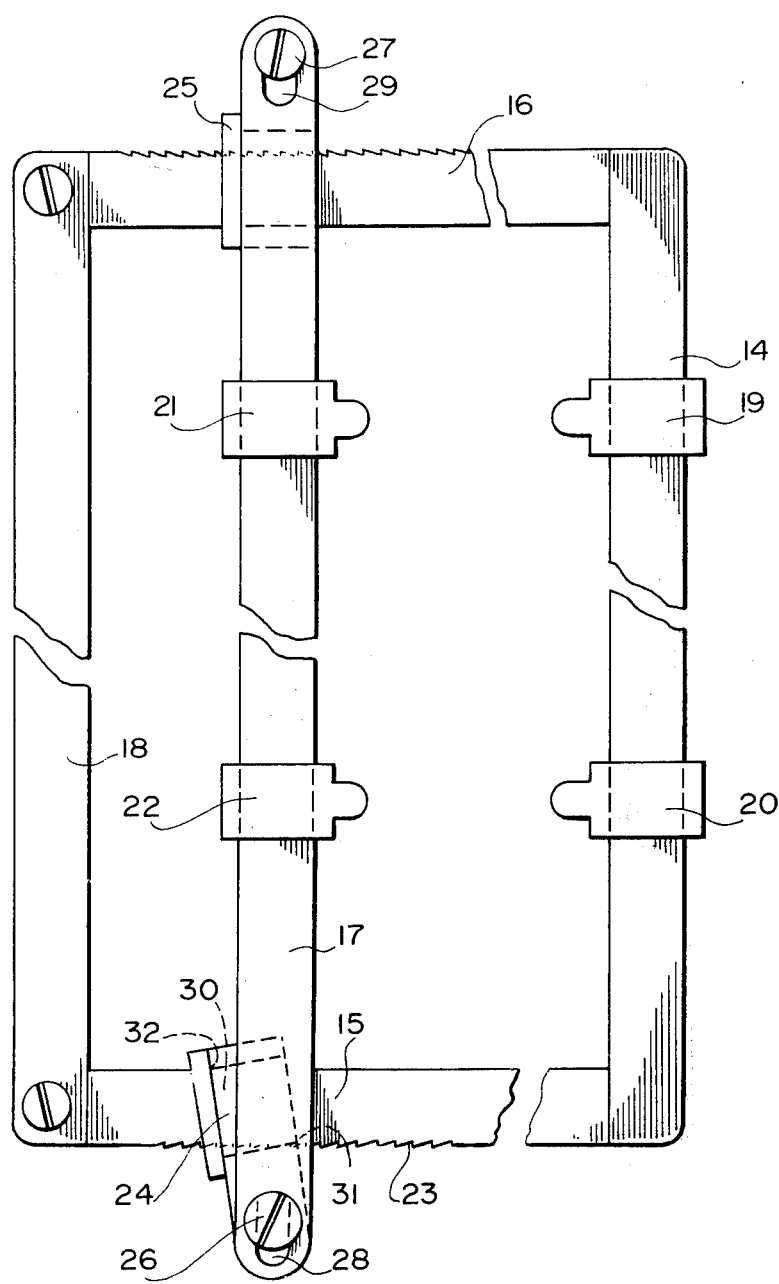
FIG. 5 is a plan view of the frame.

Each of the members 15 and 16 has teeth 23 along the outer face thereof, such teeth being pointed away from member 14. The member 17 has locking members 24 ad 25 mounted at the opposite ends thereof on pivot pins 26 and 27 respectively, these pins being slidable in slots 28 and 29 in the member 17. Each locking member is in the form of a block having a passage 30 extending therethrough of sufficient width to accommodate one of the members 15, 16 and with some play. Thus, when the surgeon has made the incision he may insert the hooks thereinto with the members 14 and 17 closely spaced and he may then simply push the members 14 and 17 apart until he has achieved the desired width of wound. The stretched musculature around the wound will, of course, attempt to bring the members 14 and 17 together again but, as shown in FIG. 5, the pull on hooks 21 and 22 will effect a pivoting action of the locking members relative to the frame member 17, thus bringing the edge 31 of passageway 30 into contact with the teeth 23 and bringing the diagonally opposite edge 32 into contact with the inner face of the frame member 15, 16 which passes through the passageway. The engagement of the edge 31 with one of the teeth 23 holds the frame member 17 in its adjusted position. Of course, after the operation has been completed and the surgeon wishes to close the wound, he simply exerts pressure on the member 17 and the locking members to bring them into position shown as occupied by member 25 in FIG. 5 and he can then simply slide the two members 14 and 17 together again and remove the frame from the patient.

Returning again to FIG. 3, it can be seen that two clamps 33 and 34 can be mounted on frame members 15 and 16 respectively to hold surgical aids 35 and 36 by their handle portions with their body portions extending into the surgical site to retain surgical matter, as required. Each of the surgical aids has a metallic core in the form of intertwined wires 37 in the handle and loops 38 in the body portion. The handle is of square cross-section and the body portion is in the form of a substantially rectangular flat pad.

Figure 4:
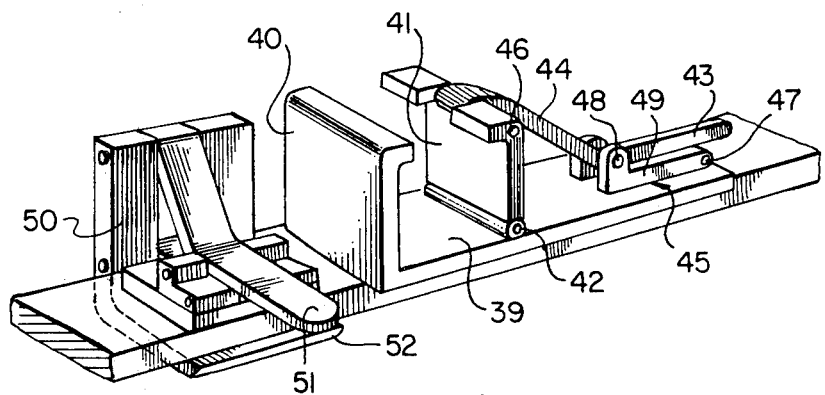
FIG. 4 is a perspective view of a clamp used with the frame shown in FIG. 3.

Referring now to FIG. 4, a clamp is shown therein which is easily manipulated by the surgeon and which can be easily adjusted along the frame member to which the surgeon wishes to attach it. The clamp comprises a base portion 39, a fixed jaw 40 extending upwardly from one end of the base portion and a movable jaw 41 pivotally mounted at 42 on the base portion. The movable jaw is moved between opened and closed positions by means of a lever 43 which is attached to one member 44 of a knee linkage 45 which is pivotally attached at 46 to the top of the jaw 41 and is pivotally attached at its other end at 47 to the base 39. The pivot 48 between the two members 44 and 49 of the knee linkage is moved over-center by actuation of the lever 43 either upwardly to open the clamp, or downwardly to close the clamp. It will be appreciated, therefore, that it is a simple matter for the surgeon to place the handle of the surgical aid between the jaws of the clamp when they are in open position and then simply depress the lever 43 with his thumb to secure the surgical aid in proper position. The clamp can be mounted on a frame member at any desired location by means of securing mechanism 50 which operates on a principle similar to that used in the clamp so that again it is a simple matter of the surgeon depressing lever 51 to secure the clamp in its desired position on the frame. The fixed jaw 52 of the securing mechanism may have a padded surface facing the frame member so as to adjust to different thicknesses of frame member and to give a secure grip thereon.

FIG. 6 shows an actual surgical site with the frame 13 in position, the hooks 19 and 20 engaging the musculature 53 around the edge of the site, one surgical aid 54 holding the bladder 55 open, it having been incised at 56, and another surgical aid 57 holding back the intestine 58 with the vertebrae 59 below it. It will be seen that each of the surgical aids specially adapted to its own function. The surgical aid shown retracting intenstine 58 is positioned to highlight an important feature of the invention. As is seen, the handle, because of its construction, is free to bend, and is bent, downwardly, i.e., toward the direction at a right angle to the direction of the handle's longitudinal axis, and also is free to bend, and is bent in a sideways direction, i.e., toward the direction at right angles to the direction of the handle's longitudinal axis and also to the downward direction. Because of this bending freedom, any bend may be made in a resultant direction in three-dimensional space the resolution of which consists of the aforementioned orthogonal directions. Thus, at any region along the handle, the handle may be bent so that a farther point on the handle or on the body can assume any location in three-dimensional space that is desired. In this way complete freedom is provided to position the handle or body in every possible location and configuration required by the surgical site and by the intestine that is retracted even though one end of the handle is fixedly secured outside the surgical site. The only positional limitations imposed are those due to the size of the surgical aid and to the location at which it is fixedly secured. Moreover, the latter constraint is variable by operation of the clamp and frame to which the handle is secured.

In short, the handle may be bent as freely as a length of cooked spaghetti, but unlike spaghetti the handle firmly retains the shape into which it is bent until a subsequent bending. This analogy may be appreciated as valid by considering the construction of the handle. The silicone elastomer polymer portion of the handle has an unrestricted bending capability and may easily be bent, for example, into a full circle. The malleable metallic core portion of the handle similarly has an unrestricted bending capability and may readily be bent into a full circle. The handle as a whole, therefore, has an unrestriced bending capability. It may be bent into a full circle, if desired, in the horizontal plane or in the vertical plane or in any planar orientation intermediate the horizontal and vertical. The foregoing obtains, it will be appreciated, even with one end of the handle fixedly clamped to the frame.

FIG. 7 shows an embodiment of the surgical aid of the invention wherein the metallic core is in the form of a solid piece of metal 60, a coil 61 of metal extending upwardly within the handle and a plurality of wires 62 radiating outwardly from the solid piece 60 into the body portion of the surgical aid. The wires 62 may be tapered as they extend away from the solid piece 60 so as to impart increased malleability (bending capability) to the body of the aid.

FIGS. 8 and 9 show another embodiment of the surgical aid wherein the body 1 has flaps 63 at the lower edge thereof, further flaps 64 at the upper edge thereof and transversely extending tabs 65 at each side edge thereof. The flaps 63 and 64 are provided with grooves 66 so that they may be more readily bent in the direction indicated by the arrow than in the opposite direction. The flaps allow for adjustment to various surgical spaces and to retain tissue. The tabs 65 perform the same function. The flaps and tabs are free of metallic core and thus have a cushioning effect upon the tissues with which they come in contact.

Figure 10:
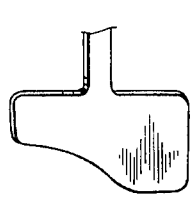
FIGS. 10 to 19 show various other embodiments of the surgical aid.
Figure 11:
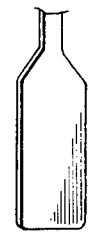
Figure 12:
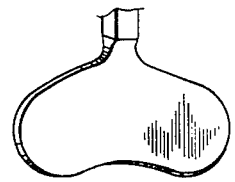
Figure 13:
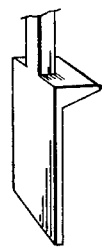
Figure 14:
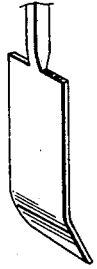
Figure 15:
Figure 16:
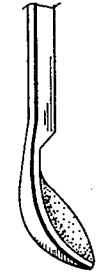
Figure 17:
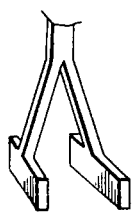
Figure 18:
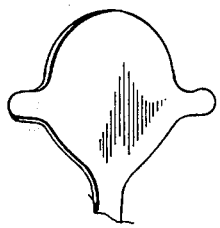
Figure 19:
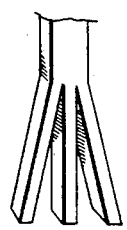

FIGS 10 to 19 show various other embodiments of the surgical aid of the present invention, each of which is adapted for a special function. Thus, FIG. 10 illustrates a surgical aid specially adapted for retaining intestine in gall bladder surgery. FIG. 11 shows an aid specially adapted for use in brain surgery and has one side heavily cushioned with a soft elastomer. FIG. 12 shows an aid adapted to retain the lung in thoracic aorta surgery. Its handle has increased strength to resist the pressure of the lung. FIG. 13 shows an aid adapted to retain the liver and the projecting edge on the top of the body portion engages the lobe of the liver. FIG. 14 shows an aid specially adapted for muscle retraction. FIG. 15 shows a long-handled oesophagus retainer for use in abdominal approaches. It is adapted for entering the abdominal cavity, coursing along the diaphragm and then curling around the oesophagus. FIG. 16 shows a surgical aid which is adapted to retain a closed bladder whereas FIG. 17 shows an aid adapted for retaining open an incised bladder, as in FIG. 6. FIG. 18 shows a surgical aid adapted for holding the base of the lung away from the diaphragm, in hiatus hernia surgery, and FIG. 19 shows an aid specially adapted to hold the heart during such surgery.

It will be apparent that surgical aids according to the invention can be used for all body cavity surgery, for example, heart, chest, brain or abdominal surgery. The invention, of course, can also be used in veterinary surgery and dentistry. Rather than have the operating surgeon displace material to a desired position and then have an assistant hold it there, moving the material on command, the surgical aids of the present invention, in combination with the described frame, allow the surgeon to arrange the surgical site exactly to his own liking and to adjust from time to time as the need arises. Moreover, because of the low profile and minimum space occupied by the frame and aids, there is much more manoeuvrability afforded the surgeon even outside the actual surgical site. The surgical aids of the invention can be manipulated to follow closely the contours of the material displaced and protect such material from air, loss of moisture, or heat, or damage from surgical tools. Moreover, they are ideal for use in, for example, brain surgery where electrically conductive materials might acutely inflame the displaced material.

Rigid, inflexible instruments may, by inadvertent action of a holding assistant, cause rupture to organs such as the liver and the spleen whereas the aids of the present invention will gently yield to avoid such rupture. Moreover, heart and intestinal cells constantly in motion may be damaged with materials that have a high frictional or abrasive surface. This will not occur with the low friction surface of the present aids.

What I claim as my invention is:

1. A surgical retractor comprising an elongated body of polymeric material having a polymeric surface which is non-toxic to cells and characterized in being three-dimensionally deformable merely by bending and without torsional deformation, with one end of said retractor fixedly secured at a point in space, into a full circle the plane of which may be in any angular orientation relative to said point in space.

2. A surgical retractor for use in retraction of parts of the patient's body during surgery, comprising:
   a. an elongated portion which is bendable as an integral part of said retractor at any region along said elongated portion without torsional deformation in each of two directions at right angles to each other and to the direction of the longitudinal axis of said elongated portion in said region, and which retains the shape of the bend produced;
   b. said portion including an elongated body of polymeric material having a surface which is polymeric and non-toxic to cells.

3. A surgical retractor as recited in claim 1 further characterized in that a plurality of said regions of said elongated portion can be so bent simultaneously.

4. A surgical retractor as recited in claim 1 wherein said elongated portion is bendable as an integral part of said device equally easily in both said two directions.

5. A surgical retractor as recited in claim 2 wherein said polymeric surface is elastomeric.

6. A surgical retractor as recited in claim 2 wherein said polymeric surface comprises a silicone elastomer.

7. A surgical retractor as recited in claim 2 wherein said polymeric surface comprises a dimethyl polysiloxane polymer.

8. A surgical retractor as recited in claim 2 wherein said polymeric surface is a poor heat conductor and a poor electrical conductor.

9. A surgical retractor as recited in claim 2 wherein said polymeric surface is repeatably sterilizable.

10. A surgical retractor as recited in claim 2 wherein said elongated portion further comprises an elongated metallic core.

11. A surgical retractor as recited in claim 10 wherein the metal of said metalic core is selected from the group consisting of aluminum, aluminum alloy and stainless steel.

12. A surgical retractor as recited in claim 10 wherein said metallic core is an elongated coiled wire.

13. A surgical retractor as recited in claim 10 wherein said elongated metallic core comprises a plurality of intertwined wires.

14. A surgical retractor as recited in claim 10 wherein said elongated metallic core is bendable at any region along its length in each of two directions at right angles to each other and to the direction of its longitudinal axis in said region and retains the shape of the bend produced.

15. A surgical retractor as recited in claim 10 wherein said elongated portion forms a handle and said surgical retractor has a body portion at one end of said handle and integral therewith, said body portion being bendable and retentive of the shape of the bend produced and having a polymeric surface which is non-toxic to cells.

16. A surgical retractor as recited in claim 15 in which said body portion contains a solid piece of metal, a coiled wire extending from said solid piece of metal into said handle and outwardly tapering wires radiating from said solid piece of metal into said body portion away from said handle.

17. A surgical retractor as recited in claim 2 wherein said elongated body of polymeric material has a rectangular cross-section transverse to said longitudinal axis of said elongated portion.

18. A surgical retractor as recited in claim 17 wherein said rectangular cross-section is square.

19. A surgical retractor as recited in claim 2 wherein said elongated portion forms a handle and said surgical retractor has a body portion at one end of said handle integral therewith, said body portion being bendable and retentive of the shape of the bend produced and having a polymeric surface which is non-toxic to cells.

20. A surgical retractor as recited in claim 19 wherein said body portion has an edge of polymeric material which itself is bendable but does not retain the shape of the bend produced in said edge.

21. A surgical retractor as recited in claim 19 wherein said polymeric surface of said body is a poor conductor of heat and electricity.

22. A surgical retractor as recited in claim 19 wherein said polymeric surface of said body is elastomeric.

23. A surgical retractor as recited in claim 19 wherein said polymeric surface of said body comprises a silicone elastomer.

24. A surgical retractor as recited in claim 19 wherein said body portion has an elongated metallic member disposed therein which is bendable at any region along said elongated metallic member's length and which retains the shape of the bend produced.

25. A surgical retractor as recited in claim 24 wherein the ease with which said elongated metallic member in said body can be bent increases along its length away from said handle.

26. A surgical retractor as recited in claim 19 wherein a first plurality of flaps extend from an edge of said body portion remote from said handle, a second plurality of flaps extend from an edge of said body portion adjacent said handle and small tabs extend laterally from the two edges extending between the first-mentioned edges.

27. A surgical retractor as recited to claim 19 wherein said body portion has small ridges on parts thereof to facilitate manipulation of said parts in the surgical site.

28. A surgical retractor as recited in claim 19 wherein said body portion has flaps thereon which have at least one groove on one face thereof to render said flaps more easily moveable in one direction than in the opposite direction.

29. A surgical retractor as recited in claim 19 wherein said body portion is divided into a plurality of independently bendable fingers.

30. A surgical retractor as recited in claim 2, in combination with a frame adapted to be mounted fixedly around a surgical site and having a clamp thereon adapted to secure a part of said elongated portion of said surgical retractor.

31. A surgical retractor as recited in claim 2 wherein said elongated portion is bifurcated at one end.

32. A method of using the surgical retractor recited in claim 19, comprising the steps of:
 a. securing one end of said handle outside a surgical site;
 b. first bending the other end of said handle toward the surgical site; and then
 c. bending said body portion into said surgical site and into contact with the part of the patient's body which is to be retracted.

33. A method as recited in claim 32, wherein said first bending step includes bending said other end of said handle at least partially in each of two directions at right angles to each other and to the direction of the longitudinal axis of said handle.

34. A surgical retractor for use in retraction of parts of the patient's body during surgery, comprising:
 a. a handle which is bendable as an integral part of said retractor at any region along said handle in each of two directions at right angles to each other and to said handle's longitudinal axis in said region, and which retains the shape of the bend produced;
 b. said handle having a surface which is polymeric and non-toxic to cells; and
 c. a body portion at one end of said handle and integral therewith;
 d. said body portion being bendable and retentive of the shape of the bend produced and having a polymeric surface which is non-toxic to cells.

35. A surgical retractor as recited in claim 34 wherein said body portion has an edge of polymeric material which itself is bendable but does not retain the shape of the bend produced in said edge.

36. A surgical retractor as recited in claim 34 wherein said polymeric surface of said body is a poor conductor of heat and electricity.

37. A surgical retractor as recited in claim 34 wherein said polymeric surface of said body is elastomeric.

38. A surgical retractor as recited in claim 34 wherein said polymeric surface of said body comprises a silicone elastomer.

39. A surgical retractor as recited in claim 34 wherein said body portion has an elongated metallic member disposed therein which is bendable at any region along said elongated metallic member's length and which retains the shape of the bend produced.

40. A surgical retractor as recited in claim 39 wherein the ease with which said elongated metallic member in said body can be bent increases along its length away from said handle.

41. A surgical retractor as recited in claim 34 wherein a first plurality of flaps extend from an edge of said body portion remote from said handle, a second plurality of flaps extend from an edge of said body portion adjacent said handle and small tabs extend laterally from the two edges extending between the first-mentioned edges.

42. A surgical retractor as recited in claim 34 wherein said body portion has small ridges on parts thereof to facilitate manipulation of said parts in the surgical site.

43. A surgical retractor as recited in claim 34 wherein said body portion has flaps thereon which have at least one groove on one face thereof to render said flaps more easily moveable in one direction than in the opposite direction.

44. A surgical device as recited in claim 34 wherein said body portion is divided into a plurality of independently bendable fingers.

45. A surgical retractor as recited in claim 34 wherein said handle includes an elongated metallic core.

46. A surgical retractor as recited in claim 45 in which said body portion contains a solid piece of metal, a coiled wire extending from said solid piece of metal into said handle and outwardly tapering wires radiating from said solid piece of metal into said body portion away from said handle.

* * * * *

UNITED STATES PATENT AND TRADEMARK OFFICE
CERTIFICATE OF CORRECTION

PATENT NO. : 4,048,987
DATED : September 20, 1977
INVENTOR(S) : James Kevin HURSON It is certified that error appears in the above-identified patent and that said Letters Patent are hereby corrected as shown below:

Column 1, line 1, in the Title, change "ACID" to -- AID --.

Column 1, line 28, after "on", change "he" to -- the --.

Column 1, line 41, change "May" to -- Many --.

Column 4, line 35, change "ad" to -- and --.

Column 5, line 42, after "aids", insert -- is --.

Column 7, Claims 3 & 4, change "claim 1" to -- claim 2 --.

Column 7, Claim 11, last line in column, change "metalic" to -- metallic --.

Signed and Sealed this

Eighth Day of August 1978

[SEAL]

Attest:

RUTH C. MASON
Attesting Officer

DONALD W. BANNER
Commissioner of Patents and Trademarks